United States Patent
Volker et al.

(10) Patent No.: US 7,141,380 B2
(45) Date of Patent: Nov. 28, 2006

(54) ASSESSMENT OF LIVER FIBROSIS SCORING WITH SERUM MARKER ALGORITHMS

(76) Inventors: Michael Volker, Ubierring 44, D-50678 Köln (DE); Michael Becka, Erienweg 5, D-59469 Ense (DE); Werner Kroll, Pfaffenberger Weg 310, D-42659 Solingen (DE); Andreas Knorr, Trillser Graben 10, D-40699 Erkrath (DE); Mathias Gehrmann, Alte Landstr. 140, D-51373 Leverkusen (DE); Guido Hennig, Nerzweg 17, 50859 Köln (DE); Sylvia Unger, Wedestr. 42, D-69420 Heidelberg (DE); Elmar-Reinhold Burchardt, Dorfstr. 28, D-58239 Schwerte (DE); Michael J. Arthur, Slab Farm, Slab Lane, West Wellow Hampshire S051 6BY (GB); Alastair D. Burt, The Gables, Fairmoor Morphet Northumberland NE 613 JL (GB); Massimo Pinzani, Via Stefano Ussi 54, I-50018 Scandicci (IT); Detlef Schuppan, Baumzeil 2, D-91088 Bubenreuth (DE)

( * ) Notice: Subject to any disclaimer, the term of this patent is extended or adjusted under 35 U.S.C. 154(b) by 382 days.

(21) Appl. No.: 10/258,689

(22) PCT Filed: Apr. 26, 2001

(86) PCT No.: PCT/EP01/04696

§ 371 (c)(1),
(2), (4) Date: Oct. 7, 2003

(87) PCT Pub. No.: WO01/86304

PCT Pub. Date: Nov. 15, 2001

(65) Prior Publication Data

US 2004/0053242 A1 Mar. 18, 2004

(51) Int. Cl.
*G01N 33/53* (2006.01)
(52) U.S. Cl. ...................................... 435/7.1
(58) Field of Classification Search .................. 435/7.1
See application file for complete search history.

(56) References Cited

OTHER PUBLICATIONS

Pilette et al (Journal of Hepatology vol. 28, pp. 439-446, 1998).*

* cited by examiner

*Primary Examiner*—Mark Navarro
(74) *Attorney, Agent, or Firm*—Rupa Sen

(57) ABSTRACT

The present invention concerns a method for diagnosing liver fibrosis wherein two or more diagnostic markers are measured and the measurements are correlated by a mathematic algorithm characterized in that the diagnostic markers are selected from the group N-terminal procollagen III propeptide (PIIINP), Collagen IV, Collagen VI, Tenascin, Laminin, Hyaluronan, MMP-2, TIMP-1 and MMP-9/TIMP-1 complex. The algorithm can be used to predict the histological score of a liver biopsy.

19 Claims, No Drawings

ASSESSMENT OF LIVER FIBROSIS SCORING WITH SERUM MARKER ALGORITHMS

RELATED APPLICATIONS

This application was filed pursuant to 35 U.S.C. § 371 and claims priority from PCT patent application Ser. No. PCT/EP01/04696, filed Apr. 26, 2001, EP Patent Application EP 1150123A1, filed Apr. 28, 2000, and Italian Patent Application 2001A000813, filed Apr. 13, 2001.

Progressive fibrotic diseases of the liver are a major cause of morbidity and mortality throughout the world. Recent scientific advances demonstrate that the pathogenic process of fibrosis in liver is critically dependent on proliferation and activation of hepatic stellate cells (also called lipocytes, fat-storing or Ito cells) which synthesize and secrete excess extracellular matrix proteins (1). Moreover it is evident that this process is common to liver disease of all aetiologies. Of particular importance are chronic viral hepatitis B and C and alcoholic liver disease as well as autoimmune and genetic liver diseases, all of which lead to clinical problems via the common final pathway of progressive liver fibrosis, with the eventual development of cirrhosis.

An important concept is the distinction between hepatic fibrosis and cirrhosis. Hepatic fibrosis is a reversible accumulation of extracellular matrix in response to chronic injury in which nodules have not yet developed, whereas cirrhosis implies an irreversible process, in which thick bands of matrix fully encircle the parenchyma, forming nodules. Consequently, any therapy must be directed towards patients with reversible disease (fibrosis), which will require early identification and monitoring of those at risk (2).

Severity and progression of liver fibrosis are difficult to assess, with liver biopsy currently remaining the most reliable clinical method. The qualitative evaluation of hepatic fibrosis by biopsies is limited by interobserver variability. Biopsies are clearly inadequate for the early clinical phase of drug development, where there is an imperative to employ less invasive methods that identify effective compounds within a commercially acceptable time frame, usually measured in weeks to a maximum of three months of experimental therapeutic exposure. Further disadvantages are the low diagnostic specificity and the risk of bleeding. Therefore there is a need for surrogate markers of liver fibrosis. Serum tests allow a non-invasive assessment of fibrogenesis and fibrolysis in the liver and can be done repeatedly and at short time intervals (3). Serum tests measuring the dynamic processes of extracellular matrix synthesis (fibrogenesis) and extracellular matrix degradation (fibrolysis) reflect the amount of extracellular matrix present, the degree of fibrosis or the ongoing process of architectural change of the liver (4).

The current state of the art in measuring surrogate markers of liver fibrosis is poorly developed. Previous studies have suggested that serum levels of extracellular matrix proteins (or their cleavage fragments) may be used to assess the severity and progression of liver fibrosis (4.5, U.S. Pat. No. 5,316,914, EP 0 283 779). Different serum markers have been investigated and correlations with liver biopsies and and severity of liver diseases have been found (6).

Some of the makers used for the assessment of liver fibrosis are PIIINP, Laminin, Hyaluronan, Collagen IV, TIMP-1, Tenascin, MMP-2 and Fibronectin. Markers are measured and their capability to assess liver fibrosis has been shown. Nevertheless, the diagnostic values of each single marker is not accurate and specific to assess fibrosis scores.

Therefore combinations of markers are discussed to increase the diagnostic value the simple biological index PGA combining prothrombin time (PT), serum gamma-glutamyl transpeptidase (GGT) and apolipoprotein A1 (Apo A1) and the index PGAA which includes alpha-2-macroglobulin ($A_2M$) to the PGA index have been described for the diagnosis of alcoholic liver disease in drinkers (7,8). Although the PGA and PGAA index have been combined with single serum markers (9, 10) serum markers have not been used for establishing algorithms for the assessment of liver diseases.

In this invention serum markers of the extracellular matrix are assembled together in a panel leading to a set of markers whose measurement will enable the calculation of an algorithm and the use of such a derived algorithm for the prediction of liver fibrosis histological score. For this purpose discriminant function analysis is used to determine which variables discriminate between the different fibrosis scores. The algorithms are derived from the set of markers N-terminal procollagen III propeptide (PIIINP), Collagen IV, Collagen VI, Tenascin, Laminin, Hyaluronan, MMP-2, TIMP-1 and MMP-9/TIMP-1 complex.

Generally, all new techniques have to be validated against existing standard techniques, provided there are any. The current "gold-standard" to assess fibrosis in the liver is the liver biopsy. With the biopsy, some randomly taken tissue out of the liver is cut into slices which become examined by an expert using a microscope. There are a lot of problems associated with liver biopsies inducing some uncertainty: distribution of fibrosis in the liver (clustered fibrosis and the needle might have hit regions of the liver not affected by fibrosis), failed sample preparation (e.g. not enough tissue material), and pathologist's individuality and preferences (individual assessments). Furthermore, the fibrotic state of the liver is usually described using scores and there are a lot of different, possibly incompatible scoring systems (e.g. Scheuer Score, Ishak Scores, etc.).

For example, in a study with 24 patients, two independent pathologists had to score the same biopsy samples for each patient at two different time-points using two different scoring systems. The number of assessments where the two pathologists came to identical results ranged from only 36% to 46%.

The new technique is based on measuring serum parameters, which are directly associated with the fibrotic process, and combining them on a mathematical level yielding a fixed assessment procedure.

In order to validate the new technique the "gold-standard" is not the best but the only mean, since a priori both methods do not investigate comparable endpoints: whereas the serum parameters characterize dynamic processes, the biopsy characterizes the fibrotic manifestation at a fixed time-point. There may be a highly active fibrotic process in the liver although fibrotic tissue has not yet been developed. In contrast, there may be large clusters of fibrotic tissue in the liver but the fibrotic activity stopped or discontinued temporarily.

Although, some mathematical functions of serum parameters yielded statistically significant different mean values in different biopsy score stages. Discriminant analyses using the "gold-standard" were chosen in order to investigate the diagnostic power of those mathematical functions of serum parameters.

Determination of concentrations of serum markers and subsequent calculation of an algorithm can also be used to make decisions whether or not a biopsy has to be taken and whether treatment should be started or continued or stopped. Therefore assignment of patients into a group of biopsy scores without taken a biopsy is advantageous. Categorization of patients into groups, e.g. mild versus serious fibrosis, by using algorithms is a benefit of the invention described.

DESCRIPTION OF THE IMMUNOASSAYS

The markers N-terminal procollagen III propeptide (PII-INP), Collagen IV, Collagen VI, Tenascin, Laminin, Hyaluronan, MMP-2, TIMP-1 and MMP-9/TIMP-1 complex are used for algorithms.

The markers are measured by making use of sandwich immunoassays. The immunoassays of the invention comprises reaction of two antibodies with human fluid samples, wherein the capture antibody specifically binds to one epitope of the marker. The second antibody of different epitope specificity is used to detect this complex. Preferably the antibodies are monoclonal antibodies and both antibodies of said two antibodies of the assay specifically bind to the protein.

Antibody or other similar term used herein includes a whole immunoglobulin either monoclonal or polyclonal as well as antigenic fragments or immunoreactive fragments which specifically bind to the marker, including Fab, Fab', $F(ab')_2$ and F(v). Antibody includes also binding-proteins, especially Hyaluronic acid binding protein (HABP).

The human fluid samples used in the assays of the invention can be any samples that contain the markers, e.g. blood, serum, plasma, urine, sputum or broncho alveolar lavage (BAL). Typically a serum or plasma sample is employed.

Antibodies of the invention can be prepared by techniques generally known in the art, and are typically generated to a sample of the markers.

The second antibody is conjugated to a detector group, e.g. alkaline phosphatase, horseradish peroxidase, or a fluorescence dye. Conjugates are prepared by techniques generally known in the art.

Concentration of the markers in human fluids are measured and algorithms calculated to assess the degree of fibrosis.

STATISTICAL BACKGROUND

Discriminant function analysis is used to determine which variables discriminate between two or more naturally occurring groups. Computationally, it is very similar to analysis of variance. The basic idea underlying discriminant function analysis is to determine whether groups differ with regard to the mean of a variable, and then to use that variable to predict group membership (e.g., of new cases). Stated in this manner, the discriminant function problem can be rephrased as a one-way analysis of variance (ANOVA) problem. Specifically, one can ask whether or not two or more groups are significantly different from each other with respect to the mean of a particular variable. If the means for a variable are significantly different in different groups, then we can say that this variable discriminates between the groups. In the case of a single variable, the final significance test of whether or not a variable discriminates between groups is the F test. F is essentially computed as the ratio of the between-groups variance in the data over the pooled (average) within-group variance. If the between-group variance is significantly larger then there must be significant differences between means.

Usually, one includes several variables in a study in order to see which one(s) contribute to the discrimination between groups. In that case, we have a matrix of total variances and co-variances; likewise, we have a matrix of pooled within-group variances and co-variances. We can compare those two matrices via multivariate F tests in order to determined whether or not there are any significant differences (with regard to all variables) between groups. This procedure is identical to multivariate analysis of variance or MANOVA As in MANOVA, one could first perform the multivariate test, and, if statistically significant, proceed to see which of the variables have significantly different means across the groups. Thus, even though the computations with multiple variables are more complex, the principal reasoning still applies, namely, that we are looking for variables that discriminate between groups, as evident in observed mean differences.

For a set of observations containing one or more quantitative variables and a classification variable defining groups of observations, the discrimination procedure develops a discriminant criterion to classify each observation into one of the groups. Post hoc predicting of what has happened in the past is not that difficult. It is not uncommon to obtain very good classification if one uses the same cases from which the discriminant criterion was computed. In order to get an idea of how well the current discriminant criterion "performs", one must classify (a priori) different cases, that is, cases that were not used to estimate the discriminant criterion. Only the classification of new cases allows us to assess the predictive validity of the discriminant criterion. In order to validate the derived criterion, the classification can be applied to other data sets. The data set used to derive the discriminant criterion is called the training or calibration data set.

The discriminant criterion (function(s) or algorithm), is determined by a measure of generalized squared distance. It can be based on the pooled co-variance matrix yielding a linear function. Either Mahalanobis or Euclidean distance can be used to determine proximity.

For the development of a discriminant algorithm, data of a group of subjects of an observational liver fibrosis of study were analyzed. Liver fibrosis scoring systems under view were the Scheuer Score (0–4), the Modified Ishak Score (HAI) A—Interface Hepatitis (0–4), the Modified Ishak Score (HAI) B—Confluent Necrosis (0–6), the Modified Ishak Score (HAI) C—Spotty Necrosis (0–4), the Modified Ishak Score (HAI) D—Portal Inflammation (0–4), the Modified HAI Score (Ishak Score)(0–6).

Applying a stepwise discriminant analysis, for example the following functions of serum parameters showed to have major impact on the corresponding scoring type.

| Scoring Type | Surrogate Parameters | | |
|---|---|---|---|
| Scheurer Score: | ln(TIMP -1) | ln(Collagen VI/ Hyaluronan) | ln(Hyaluronan/ Laminin) |
| Modified Ishak Score A - Interface Hepatitis: | ln(TIMP-1) | ln(Collagen VI/ Hyaluronan) | ln(Collagen VI/ Tenascin) |
| Modified Ishak Score B - Confluent Necrosis: | ln(Hyaluronan) | ln(Collagen VI/ MMP-2) | |
| Modified Ishak Score C - Spotty Necrosis: | ln(Hyaluronan) | ln(MMP-9/TIMP-1/ complex Tenascin) | |
| Modified Ishak Score D - Portal Inflammation: | ln(Laminin) | ln(Collagen VI/ TIMP-1) | |
| Modified Ishak Score - Stage: | ln(TIMP-1) | ln(Collagen VI/ Hyaluronan) | ln(Hyaluronan/ Laminin) |

A corresponding discriminant analysis yielded the linear discriminating functions which can be used for calculation and prediction of biopsy score. The algorithms can be applied to every known scoring system (e.g. Scheuer Score, Ishak Score, Netavir Score, Ludwig Score, HAI Score).

Algorithms can be used to predict the biopsy score of a patient (e.g. score 0, 1, 2, 3, . . . ) or to predict a group of scores (category) a patient belongs to (e.g. mild fibrosis; score 0 to 1).

Discriminating functions used includes combinations of markers from the list of N-terminal procollagen III propeptide (PIIINP), Collagen IV, Collagen VI, Tenascin, Laminin, Hyaluronan, MMP-2, TIMP-1 and MMP-9/TIMP-1 complex and also factors between −1000 and +1000.

Different scores need different algorithm form the list of markers and factors.

EXAMPLES

Example 1

Algorithms for Scheuer Score

The following algorithms 1, 2 and 3 were calculated by correlating biopsies assessed by the Scheuer scoring system and serum marker concentrations of a group of patients with liver diseases:

Algorithm 1:

| [0] | −108.861 + 0.283 * LOG(COL_VI/HYAL) − 1.050 * LOG(HYAL/LAM) + 35.372 * LOG(TIMP1) |
| [1] | −114.231 + 0.195 * LOG(COL_VI/HYAL) − 0.654 * LOG(HYAL/LAM) + 36.158 * LOG(TIMP1) |
| [2] | −120.649 − 0.998 * LOG(COL_VI/HYAL) − 2.102 * LOG(HYAL/LAM) + 36.925 * LOG(TIMP1) |
| [3] | −123.672 − 1.281 * LOG(COL_VI/HYAL) − 1.344 * LOG(HYAL/LAM) + 37.163 * LOG(TIMP1) |
| [4] | −133.207 − 2.186 * LOG(COL_VI/HYAL) − 1.602 * LOG(HYAL/LAM) + 38.188 * LOG(TIMP1) |

Algorithm 2:

| [0] | −75.18797 + 23.04542 * LOG(TIMP1) − 0.583641 * LOG(COL_VI/HYAL) − 0.140956 * LOG(HYAL/LAM) |
| [1] | −76.1526 + 23.15895 * LOG(TIMP1) − 0.963402 * LOG(COL_VI/HYAL) − 0.009472 * LOG(HYAL/LAM) |
| [2] | −78.62662 + 23.32161 * LOG(TIMP1) − 1.227332 * LOG(COL_VI/HYAL) − 0.067969 * LOG(HYAL/LAM) |
| [3] | −83.09285 + 23.64493 * LOG(TIMP1) − 2.181493 * LOG(COL_VI/HYAL) − 0.300241 * LOG(HYAL/LAM) |
| [4] | −93.89732 + 24.86246 * LOG(TIMP1) − 2.841299 * LOG(COL_VI/HYAL) − 0.136885 * LOG(HYAL/LAM) |

Algorithm 3:

| [0] | −95.39661 + 17.66025 * LOG(HYAL) − 0.820836 * LOG(COL_IV) + 0.245778 * LOG(COL_VI/PIIINP) − 17.79663 * LOG(COL_VI/TIMP1) − 14.96754 * LOG(HYAL/MMP2) − 0.279356 * LOG(LAM/MMP9T) |
| [1] | −95.84457 + 17.62365 * LOG(HYAL) − 0.667854 * LOG(COL_IV) + 0.155707 * LOG(COL_VI/PIIINP) − 18.0407 * LOG(COL_VI/TIMP1) − 14.42688 * LOG(HYAL/MMP2) − 0.554323 * LOG(LAM/MMP9T) |
| [2] | −99.13575 + 17.76656 * LOG(HYAL) − 0.978731 * LOG(COL_IV) − 0.12995 * LOG(COL_VI/PIIINP) − 18.69948 * LOG(COL_VI/TIMP1) − 14.49353 * LOG(HYAL/MMP2) − 0.647247 * LOG(LAM/MMP9T) |
| [3] | −104.4554 + 18.38886 * LOG(HYAL) − 0.202832 * LOG(COL_IV) − 0.157058 * LOG(COL_VI/PIIINP) − 18.70409 * LOG(COL_VI/TIMP1) − 14.49716 * LOG(HYAL/MMP2) − 0.340197 * LOG(LAM/MMP9T) |
| [4] | −119.8887 + 20.14719 * LOG(HYAL) + 0.959792 * LOG(COL_IV) − 0.80876 * LOG(COL_VI/PIIINP) − 18.69873 * LOG(COL_VI/TIMP1) − 15.57103 * LOG(HYAL/MMP2) − 0.229757 * LOG(LAM/MMP9T) |

The algorithm were used to predict biopsy scores of a separate group of patients. The calculated scores were compared with scores determined by a single pathologist (case B), with a consensus score of 3 pathologists (case C) and with the range covered by all pathologists (case A). Kappa values, negative predictive values (NPV) for score 0–1, positive predictive values (PPV) for score 2–4, sensitivities and specificities have also been calculated.

|  | Algorithm 1 | | | Algorithm 2 | | | Algorithm 3 | | |
| --- | --- | --- | --- | --- | --- | --- | --- | --- | --- |
|  | C | A | B | C | A | B | C | A | B |
| Hit-Rate (%) [0] | 33.3 | 38.9 | 35.0 | 17.1 | 40.0 | 13.7 | 20.0 | 41.4 | 16.8 |
| Hit-Rate (%) [1] | 36.8 | 42.7 | 36.0 | 80.7 | 81.6 | 75.8 | 74.6 | 77.2 | 71.7 |
| Hit-Rate (%) [2] | 25.8 | 42.4 | 19.0 | 0.0 | 36.8 | 0.0 | 0.0 | 34.2 | 5.1 |
| Hit-Rate (%) [3] | 26.1 | 34.8 | 22.2 | 6.4 | 17.0 | 5.2 | 12.8 | 21.3 | 9.3 |
| Hit-Rate (%) [4] | 63.0 | 63.0 | 55.9 | 62.5 | 62.5 | 52.9 | 43.8 | 43.8 | 47.1 |
| Hit-Rate (%) All | 35.9 | 42.9 | 33.8 | 42.2 | 54.2 | 36.7 | 39.5 | 51.2 | 36.7 |
| N | 468 | 468 | 793 | 301 | 301 | 626 | 301 | 301 | 626 |
| Kappa | 0.175 | 0.268 | 0.151 | . | 0.199 | . | 0.124 | 0.310 | 0.121 |
| L_Kappa | 0.119 | 0.211 | 0.109 | . | 0.134 | . | 0.056 | 0.235 | 0.077 |
| U_Kappa | 0.231 | 0.325 | 0.192 | . | 0.265 | . | 0.191 | 0.385 | 0.165 |
| P (Kappa = 0) | <0.0001 | <0.0001 | <0.0001 | . | <0.0001 | . | <0.0001 | <0.0001 | <0.0001 |
| NPV (%) [0–1] | 61.6 | 63.8 | 62.8 | 91.8 | 92.4 | 85.5 | 88.0 | 89.1 | 81.6 |
| PPV (%) [2–4] | 66.1 | 75.1 | 66.3 | 31.6 | 46.2 | 35.4 | 35.0 | 48.7 | 39.0 |
| Hit-Rate (%) All | 63.5 | 68.4 | 64.2 | 68.4 | 74.4 | 65.8 | 67.4 | 73.4 | 64.9 |
| Kappa | 0.268 | 0.372 | 0.280 | 0.261 | 0.417 | 0.226 | 0.252 | 0.404 | 0.219 |
| L_Kappa | 0.182 | 0.291 | 0.214 | 0.160 | 0.315 | 0.152 | 0.146 | 0.299 | 0.142 |
| U_Kappa | 0.354 | 0.454 | 0.346 | 0.363 | 0.520 | 0.300 | 0.358 | 0.508 | 0.295 |
| P (Kappa = 0) | <0.0001 | <0.0001 | <0.0001 | <0.0001 | <0.0001 | <0.0001 | <0.0001 | <0.0001 | <0.0001 |
| Sensitivity | 0.539 | 0.584 | 0.540 | 0.712 | 0.794 | 0.613 | 0.651 | 0.740 | 0.578 |
| Specificity | 0.729 | 0.791 | 0.739 | 0.679 | 0.730 | 0.671 | 0.681 | 0.732 | 0.674 |

Example 2

Algorithms for Ishak Score

The following algorithms 1, 2 and 3 were calculated by correlating biopsies assessed by the Ishak scoring system and serum marker concentrations of a group of patients with liver diseases:

Algorithm 1:

[0] −107.752 − 0.347 * LOG(COL_VI/HYAL) − 1.493 * LOG(HYAL/LAM) + 34.879 * LOG(TIMP1)
[1] −112.550 − 0.301 * LOG(COL_VI/HYAL) − 1.086 * LOG(HYAL/LAM) + 35.617 * LOG(TIMP1)
[2] −114.626 − 0.760 * LOG(COL_VI/HYAL) − 1.270 * LOG(HYAL/LAM) + 35.819 * LOG(TIMP1)
[3] −121.339 − 2.065 * LOG(COL_VI/HYAL) − 2.910 * LOG(HYAL/LAM) + 36.593 * LOG(TIMP1)
[4] −119.289 − 1.009 * LOG(COL_VI/HYAL) − 1.271 * LOG(HYAL/LAM) + 36.449 * LOG(TIMP1)
[5] −125.551 − 2.966 * LOG(COL_VI/HYAL) − 2.536 * LOG(HYAL/LAM) + 36.797 * LOG(TIMP1)
[6] −133.055 − 3.256 * LOG(COL_VI/HYAL) − 2.329 * LOG(HYAL/LAM) + 37.695 * LOG(TIMP1)

Algorithm 2:

[0] −75.94035 + 23.20826 * LOG(TIMP1) − 0.911827 * LOG(COL_VI/HYAL) − 0.295297 * LOG(HYAL/LAM)
[1] −76.0885 + 23.14058 * LOG(TIMP1) − 1.221511 * LOG(COL_VI/HYAL) − 0.155608 * LOG(HYAL/LAM)
[2] −80.17664 + 23.6506 * LOG(TIMP1) − 1.41651 * LOG(COL_VI/HYAL) − 0.210415 * LOG(HYAL/LAM)
[3] −79.12945 + 23.42277 * LOG(TIMP1) − 1.582733 * LOG(COL_VI/HYAL) − 0.175959 * LOG(HYAL/LAM)
[4] −83.24617 + 23.7777 * LOG(TIMP1) − 2.174834 * LOG(COL_VI/HYAL) − 0.311583 * LOG(HYAL/LAM)
[5] −89.60186 + 24.2615 * LOG(TIMP1) − 3.237993 * LOG(COL_VI/HYAL) − 0.914309 * LOG(HYAL/LAM)
[6] −95.5774 + 25.11333 * LOG(TIMP1) − 3.293235 * LOG(COL_VI/HYAL) − 0.347014 * LOG(HYAL/LAM)

Algorithm 3:

[0] −100.6452 + 17.18813 * LOG(HYAL) + 15.20461 * LOG(COL_IV/HYAL) + 0.515498 * LOG(COL_VI/PIIINP) + 3.309452 * LOG (LAM) − 15.47806 * LOG(COL_IV/MMP2) − 17.50773 * LOG(COL_VI/TIMP1)
[1] −98.87092 + 17.18161 * LOG(HYAL) + 14.7876 * LOG(COL_IV/HYAL) + 0.530071 * LOG(COL_VI/PIIINP) + 3.067209 * LOG (LAM) − 14.74001 * LOG(COL_IV/MMP2) − 17.62455 * LOG(COL_VI/TIMP1)
[2] −104.8869 + 17.78543 * LOG(HYAL) + 15.25944 * LOG(COL_IV/HYAL) + 0.352181 * LOG(COL_VI/PIIINP) + 3.175207 * LOG (LAM) − 15.56044 * LOG(COL_IV/MMP2) − 17.97986 * LOG(COL_VI/TIMP1)
[3] −102.8131 + 17.32281 * LOG(HYAL) + 14.69307 * LOG(COL_IV/HYAL) + 0.176959 * LOG(COL_VI/PIIINP) + 2.822227 * LOG (LAM) − 15.15272 * LOG(COL_IV/MMP2) − 18.37351 * LOG(COL_VI/TIMP1)
[4] −109.2574 + 18.44309 * LOG(HYAL) + 15.53464 * LOG(COL_IV/HYAL) − 0.152374 * LOG(COL_VI/PIIINP) + 2.957847 * LOG (LAM) − 15.02773 * LOG(COL_IV/MMP2) − 18.59138 * LOG(COL_VI/TIMP1)
[5] −116.8556 + 19.00778 * LOG(HYAL) + 15.47539 * LOG(COL_IV/HYAL) + 0.436656 * LOG(COL_VI/PIIINP) + 3.995456 * LOG (LAM) − 15.54302 * LOG(COL_IV/MMP2) − 18.53013 * LOG(COL_VI/TIMP1)
[6] −127.2084 + 21.66093 * LOG(HYAL) + 17.77795 * LOG(COL_IV/HYAL) − 0.631902 * LOG(COL_VI/PIIINP) + 3.589129 * LOG (LAM) − 16.1393 * LOG(COL_IV/MMP2) − 18.40445 * LOG(COL_VI/TIMP1)

The algorithms were used to predict biopsy scores of a separate group of patients. The calculated scores were compared with scores determined by a single pathologist (case B), with a consensus score of 3 pathologists (case C) and with the range covered by all pathologists (case A). Kappa values, negative predictive values (NPV) for score 0–2, positive predictive values (PPV) for score 3–6, sensitivities and specificities have also been calculated.

|  | Algorithm 1 | | | Algorithm 2 | | | Algorithm 2 | | |
| --- | --- | --- | --- | --- | --- | --- | --- | --- | --- |
|  | C | A | B | C | A | B | C | A | B |
| Hit-Rate (%) [0] | 28.7 | 31.5 | 29.5 | 45.7 | 58.6 | 41.0 | 45.7 | 57.1 | 39.8 |
| Hit-Rate (%) [1] | 25.0 | 34.0 | 29.2 | 50.8 | 60.7 | 50.8 | 27.9 | 41.0 | 37.7 |
| Hit-Rate (%) [2] | 10.7 | 24.0 | 9.7 | 0.0 | 22.4 | 1.1 | 1.7 | 15.5 | 1.1 |
| Hit-Rate (%) [3] | 23.0 | 27.9 | 20.2 | 0.0 | 3.1 | 0.0 | 9.4 | 12.5 | 6.9 |
| Hit-Rate (%) [4] | 22.2 | 37.8 | 25.6 | 0.0 | 0.0 | 0.0 | 0.0 | 7.7 | 3.3 |
| Hit-Rate (%) [5] | 32.0 | 44.0 | 24.4 | 4.5 | 18.2 | 2.6 | 0.0 | 18.2 | 2.6 |
| Hit-Rate (%) [6] | 57.4 | 57.4 | 51.1 | 71.9 | 71.9 | 60.9 | 43.8 | 43.8 | 52.2 |
| Hit-Rate (%) All | 27.1 | 34.6 | 27.3 | 28.9 | 39.5 | 28.1 | 22.3 | 32.6 | 25.2 |
| N | 468 | 468 | 794 | 301 | 301 | 627 | 301 | 301 | 627 |
| Kappa | 0.138 | 0.228 | 0.136 | . | . | . | 0.031 | 0.093 | 0.041 |
| L_Kappa | 0.090 | 0.177 | 0.100 | . | . | . | −0.02 | 0.039 | 0.006 |
| U_Kappa | 0.186 | 0.279 | 0.173 | . | . | . | 0.084 | 0.147 | 0.076 |
| P (Kappa = 0) | <0.0001 | <0.0001 | <0.0001 | . | . | . | 0.2293 | 0.0003 | 0.0152 |
| NPV (%) [0–2] | 57.2 | 59.4 | 59.1 | 89.9 | 91.0 | 83.9 | 77.8 | 80.4 | 75.1 |
| PPV (%) [3–6] | 71.9 | 79.5 | 74.2 | 40.2 | 50.9 | 41.5 | 47.3 | 55.4 | 48.1 |
| Hit-Rate (%) All | 63.0 | 67.3 | 65.0 | 71.4 | 76.1 | 67.6 | 66.4 | 71.1 | 64.8 |
| Kappa | 0.274 | 0.362 | 0.312 | 0.330 | 0.450 | 0.271 | 0.259 | 0.366 | 0.238 |
| L_Kappa | 0.191 | 0.283 | 0.249 | 0.223 | 0.346 | 0.195 | 0.147 | 0.257 | 0.160 |
| U_Kappa | 0.356 | 0.441 | 0.374 | 0.437 | 0.554 | 0.347 | 0.371 | 0.475 | 0.316 |
| P (Kappa = 0) | <0.0001 | <0.0001 | <0.0001 | <0.0001 | <0.0001 | <0.0001 | <0.0001 | <0.0001 | <0.0001 |
| Sensitivity | 0.524 | 0.561 | 0.537 | 0.703 | 0.770 | 0.617 | 0.558 | 0.626 | 0.547 |
| Specificity | 0.757 | 0.816 | 0.781 | 0.717 | 0.758 | 0.697 | 0.714 | 0.752 | 0.699 |

Example 3

Receiver Operating Characteristic (ROC) Curves for Scheuer Score

Grouping the patients into categories no/mild fibrosis (score 0–1) and moderate/severe fibrosis (score 2–4) for the Scheuer score and calculating algorithms for the dichotomous outcome gave the following results:

Algorithm 4:

$$\text{LOGIT} = 7.11957755 - 0.67952658\,\text{LOG (TIMP1)} + 1.01832374 * \text{LOG(COL\_VI/HYAL)} + 0.09461778 * \text{LOG(HYAL/LAM)}$$

Algorithm 5:

$$\text{LOGIT} = 8.6908419 - 0.76944684 * \text{LOG(HYAL)} - 0.47836706 * \text{LOG(COL\_IV)} + 0.43870798 * \text{LOG(COL\_VI/PIIINP)} + 0.74453459 * \text{LOG (COL\_VI/TIMP1)} + 0.05605262 * \text{LOG(HYAL/MMP2)} - 0.01871531 * \text{LOG(LAM/MMP9T)}$$

The algorithms were used to calculate receiver operating characteristic curves for the categories no/mild fibrosis (score 0–1) and moderate/severe fibrosis (score 2–4) for the Scheuer score. The calculated scores were compared with scores determined by a single pathologist (case B), with a consensus score of 3 pathologists (case C) and with the range covered by all pathologists (case A). Area under curve (AUC) values have been calculated.

|  | Algorithm 4 | | | Algorithm 5 | | |
| --- | --- | --- | --- | --- | --- | --- |
|  | C | A | B | C | A | B |
| AUC | 0.759 | 0.899 | 0.759 | 0.746 | 0.871 | 0.756 |
| N | 295 | 295 | 569 | 291 | 291 | 562 |

Example 4

Receiver Operating Characteristic (ROC) Curves for Ishak Score

Grouping the patients into categories no/mild fibrosis (score 0–2) and moderate/severe fibrosis (score 3–6) for the Ishak score and calculating algorithms for the dichotomous outcome gave the following results:

Algorithm 4:

$$\text{LOGIT} = 7.22920269 - 0.68033581 * \text{LOG(TIMP1)} + 1.04300795 * \text{LOG(COL\_VI/HYAL)} + 0.08483109 * \text{LOG(HYAL/LAM)}$$

Algorithm 5:

$$\text{LOGIT} = 8.92321331 - 1.28340678 * \text{LOG(HYAL)} - 0.54350583 * \text{LOG(COL\_IV/HYAL)} + 0.47836792 * \text{LOG(COL\_VI/PIIINP)} + 0.02076678 * \text{LOG(LAM)} + 0.07719237 * \text{LOG(COL\_IV/MMP2)} + 0.76194671 * \text{LOG(COL\_VI/TIMP1)}$$

The algorithms were used to calculate receiver operating characteristic curves for the categories no/mild fibrosis (score 0–2) and moderate/severe fibrosis (score 3–6) for the Ishak score. The calculated scores were compared with scores determined by a single pathologist (case B), with a consensus score of 3 pathologists (case C) and with the range covered by all pathologists (case A). Area under curve (AUC) values have been calculated.

|  | Algorithm 4 | | | Algorithm 5 | | |
| --- | --- | --- | --- | --- | --- | --- |
|  | C | A | B | C | A | B |
| AUC | 0.763 | 0.887 | 0.763 | 0.751 | 0.861 | 0.757 |
| N | 295 | 295 | 570 | 292 | 292 | 564 |

Literature
1. Friedman S L The cellular basis of hepatic fibrosis: Mechanism and treatment strategies. N Engl J Med 1993; 328: 1828–1835
2. Friedman S L Molecular mechanism of hepatic fibrosis and principle of therapy J Gastroenterol 1997; 32: 424–430
3. Hayasaka A, Saisho H Serum markers as tools to monitor liver fibrosis Digestion 1998; 59: 381–384
4. Schuppan D, Stolzel U, Oesterling C, Somasundaram R Serum assays for liver fibrosis. J Hepatol 1995; 22 (Suppl 2): 82–88
5. Murawaki Y, Ikuta Y, Nishimura Y, Koda M, Kawasaki H Serum markers for connective tissue turnover in patients with chronic hepatitis C: A comparative analysis. J Hepatol 1995; 23: 145–152
6. Wong V S, Hughes V, Trull A, Wight D G D, Peptrik J, Alexander G J M Serum hyaluronic acid is a useful marker of liver fibrosis in chronic hepatitis C virus infection J Viral Hepatitis 1998; 5: 187–192
7. Poynard T, Aubert A, Bedossa P, Abella A, Naveau S, Paraf F, Chapu J C A simple biological index for detection of alcoholic liver disease in drinkers Gastroenterology 1991; 100: 1397–1402
8. Naveau S, Poynard T, Benattat C, Bedossa P, Chaput J C Alpha-2 macroglobulin and hepatic fibrosis: diagnostic interest Dig Dis Sci 1994; 11: 2426–2432
9. Oberti F, Valsesia E, Pilette C, Rousselet M C, Bedossa P, Aube C, Gallois Y, Rifflet H, Maiga M Y, Penneau-Fontbonne D, Cales P Noninvasive diagnosis of hepatic fibrosis and cirrhosis Gastroenterology 1997; 113: 1609–1616
10. Teare J P, Sherman D, Greenfield S M, Simpson J, Catterall A P, Murray-Lyon I M, Peters T J, Williams R, Thompson R P H The Lancet 1993; 342: 895–898

The invention claimed is:

1. A method for aiding in the diagnosis of liver fibrosis comprising:
    (a) obtaining a sample of body fluid from an individual;
    (b) selecting two or more diagnostic markers from the group consisting of: PIIINP, Collagen IV, Collagen VI, Tenascin, Laminin, Hyaluronan, MMP-2, TIMP-1 and MMP-9/TIMP-1 complex;
    (c) measuring the amount of each said selected two or more diagnostic markers in said sample to obtain a measured value for each of said selected diagnostic markers; and
    (d) combining said measured value of each said selected diagnostic markers using a mathematical algorithm to obtain a liver fibrosis score.

2. The method according to claim 1 wherein said sample of body fluid is blood, serum, plasma or urine.

3. The method according to claim 1 wherein said liver fibrosis score is used to support, predict or substitute the histological score of a liver biopsy.

4. The method according to claim 1 wherein said mathematical algorithm is a discriminant function algorithm.

5. The method according to claim 4 wherein said discriminant function algorithm is a linear discriminant function algorithm.

6. The method according to claim 4 wherein said liver fibrosis score corresponds to a pathology score obtained by a histological assessment of a liver biopsy.

7. The method according to claim 6 wherein said pathology score is obtained by using any one of the following scoring systems: the Scheuer scoring system, the Ishak scoring system, the HAI scoring system, the Ludwig scoring system, or the Metavir scoring system.

8. The method according to claim 1 wherein said liver fibrosis score is at least one factor used to determine a treatment strategy for said individual.

9. The method according to claim 1 wherein said liver fibrosis score is at least one factor used to monitor the efficacy of an implemented treatment strategy for said individual.

10. The method according to claim 1 wherein said liver fibrosis score is at least one factor used to determine whether said individual should obtain a liver biopsy.

11. The method according to claim 1 wherein said liver fibrosis score is at least one factor used to distinguish liver fibrosis from liver cirrhosis.

12. The method according to claim 1 wherein said liver fibrosis score is at least one factor used to evaluate the degree of liver fibrosis in said individual.

13. The method according to claim 1 wherein said selected diagnostic markers includes at least one of Hyaluronan, PIIINP or TIMP-1.

14. The method according to claim 1 wherein said selected diagnostic markers includes at least two of Hyaluronan, PIIINP or TIMP-1.

15. The method according to claim 1 wherein said selected diagnostic markers includes Hyaluronan, PIIINP and TIMP-1.

16. The method according to claim 3 wherein said body fluid is blood, serum, plasma or urine.

17. The method according to claim 3 wherein said liver fibrosis score is used to support, predict or substitute the histological score of a liver biopsy.

18. The method according to claim 3 wherein said liver fibrosis score is at least one factor used to determine a treatment strategy for said individual.

19. The method according to claim 1 wherein said liver fibrosis score is at least one factor used to monitor the efficacy of an implemented treatment strategy for said individual.

* * * * *